United States Patent
Shue et al.

(10) Patent No.: US 7,678,080 B2
(45) Date of Patent: Mar. 16, 2010

(54) INTRAVENOUS CATHETER INTRODUCING DEVICE

(76) Inventors: Ming-Jeng Shue, No. 14, Lane 8, Chung-I St., Hsi Dist., Taichung City (TW); Deborah Huang, 7F, No. 5, Sec. 3, Liu-Chun E. Rd., Chung Dist., Taichung City (TW); Phillip Shue, No. 14, Lane 8, Chung-I St., Hsi Dist., Taichung City (TW)

( * ) Notice: Subject to any disclaimer, the term of this patent is extended or adjusted under 35 U.S.C. 154(b) by 142 days.

(21) Appl. No.: 11/974,943

(22) Filed: Oct. 15, 2007

(65) Prior Publication Data

US 2008/0132846 A1 Jun. 5, 2008

(30) Foreign Application Priority Data

Nov. 30, 2006 (TW) .............................. 95144386 A

(51) Int. Cl.
*A61M 5/178* (2006.01)

(52) U.S. Cl. .................. 604/164.01; 24/311; 24/335; 24/339; 24/442; 24/552; 24/634; 604/110; 604/181; 604/182; 604/183; 604/184; 604/185; 604/186; 604/187; 604/192; 604/198; 604/218; 604/220; 604/223; 604/227; 604/228; 604/229

(58) Field of Classification Search .................. 24/311, 24/335, 339, 442, 458, 551, 552, 634; 604/110, 604/181–187, 192, 198, 218, 220, 223, 227–229
See application file for complete search history.

(56) References Cited

U.S. PATENT DOCUMENTS 2,705,494 A * 4/1955 Broadwin ................... 604/210
4,556,060 A * 12/1985 Perlin ......................... 606/158
4,776,346 A * 10/1988 Beraha et al. ............... 600/567
4,998,924 A * 3/1991 Ranford ...................... 604/198
5,092,851 A * 3/1992 Ragner ....................... 604/192
5,176,656 A * 1/1993 Bayless ...................... 604/198
5,318,538 A * 6/1994 Martin ....................... 604/110
5,360,405 A * 11/1994 Yoon ..................... 604/164.12
5,464,418 A * 11/1995 Schraga ..................... 606/182
5,704,911 A * 1/1998 Parsons ....................... 604/72
5,779,679 A * 7/1998 Shaw ......................... 604/158
5,865,806 A * 2/1999 Howell .................. 604/164.12
5,873,856 A * 2/1999 Hjertman et al. ............ 604/117
6,039,713 A * 3/2000 Botich et al. ................ 604/110
6,210,371 B1 * 4/2001 Shaw .................... 604/164.08
6,679,864 B2 * 1/2004 Gagnieux et al. ........... 604/198
6,981,965 B2 * 1/2006 Luther et al. ................ 604/110
2001/0037089 A1 * 11/2001 Domici, Jr. ................. 604/192
2004/0116864 A1 * 6/2004 Boudreaux ............. 604/164.01
2005/0101917 A1 * 5/2005 Doyle ......................... 604/187

* cited by examiner

*Primary Examiner*—Nicholas D Lucchesi
*Assistant Examiner*—Scott Medway
(74) *Attorney, Agent, or Firm*—Townsend and Townsend and Crew, LLP

(57) ABSTRACT

An intravenous catheter introducing device includes a needle hub slidably inserted into a barrel and holding a needle cannula, a biasing member disposed to bias the needle hub to a rear position so as to retract the needle cannula in the barrel, and an easy release unit including an engaging wall segment which is attached to an outer surface of the barrel, two flexible squeezed wall segments which extend from the engaging wall segment and which is squeezable so as to move two latch members to steer clear of a retained end of the needle hub through an access hole in the barrel, thereby permitting the biasing member to bias the needle hub towards the rear position.

16 Claims, 18 Drawing Sheets

INTRAVENOUS CATHETER INTRODUCING DEVICE

CROSS-REFERENCES TO RELATED APPLICATIONS

This application claims priority to Taiwanese Application No. 095144386, filed Nov. 30, 2006, the disclosure of which is herein incorporated by reference.

BACKGROUND OF THE INVENTION

1. Field of the Invention

This invention relates to an intravenous catheter introducing device, more particularly to an intravenous catheter introducing device with a needle cannula which is retractable into a barrel for safe disposal.

2. Description of the Related Art

Conventional medical devices or syringes for medicine injection, drawing blood samples, etc., have to be disposed of safely after use to avoid accidental needle pricks or undesirable contamination. Although a tip protector is provided to be sleeved on the device after use to ensure that the needle is covered, the user is exposed to the risk of being pricked by the needle when sleeving the tip protector on the used device. Therefore, there are available medical devices or syringes with a retractable needle that is retractable into a barrel or a plunger after the injection operation is completed, such as those disclosed in U.S. patent application Ser. Nos. 11/488,406 and 11/488,424 filed by the applicants, and U.S. Pat. Nos. 7,044,935, 7,204,813, and 7,211,064 issued to the applicants. However, further improvements are desirable in order to ensure easy and safe retraction of the needle and to simplify the construction of medical devices or syringes.

SUMMARY OF THE INVENTION

The object of the present invention is to provide an intravenous catheter introducing device which has a simplified construction and which can be operated easily and safely to retract a used needle cannula.

According to this invention, the intravenous catheter introducing device includes a barrel having front and rear open ends opposite to each other in a longitudinal direction, and a surrounding barrel wall which interconnects the front and rear open ends. The surrounding barrel wall includes a smaller-diameter wall portion and a larger-diameter wall portion. The surrounding barrel wall has an inner barrel wall surface to confine a passage, and an outer barrel wall surface having an access hole which is formed in the larger-diameter wall portion and which extends through the inner barrel wall surface. A needle cannula has a front segment terminating at a tip end, and a rear connecting end opposite to the front segment along the axis. A needle hub includes a front holding portion surrounded by the smaller-diameter wall portion, a rear shell portion slidable relative to the surrounding barrel wall along the axis between front and rear positions which are respectively proximate to the front open end and the rear open end, and an intermediate viewing-window portion disposed between the front holding portion and the rear shell portion. The front holding portion holds the rear connecting end of the needle cannula such that, when the rear shell portion is in the front position, the needle cannula is placed in a position of use, where the front segment extends forwardly of the front open end for ready use, and when the rear shell portion is in the rear position, the needle cannula is placed in a disposal position, where the front segment retreats into the passage.

The rear shell portion extends to terminate at a retained end. The intermediate viewing-window portion defines a blood-flow passage which is in fluid communication with the needle cannula. A biasing member is interposed between the rear shell portion and the inner barrel wall surface so as to bias the rear shell portion toward the rear position. The access hole is disposed in the vicinity of the retained end in the position of use such that, by accessing the retained end through the access hole, the retained end is enabled to be held against the biasing action of the biasing member.

An easy release unit includes an engaging wall segment, left and right squeezed wall segments, and left and right latch members. The engaging wall segment is configured to attach to the outer barrel wall surface. The left and right squeezed wall segments extend from the engaging wall segment to be outboard to the outer barrel wall surface, and are opposite to each other in a first direction transverse to the longitudinal direction. The left and right squeezed wall segments extend in a second direction transverse to both the longitudinal direction and the first direction to terminate at left and right joint regions, respectively. The left and right squeezed wall segments are made of a flexible material such that upon being squeezed towards each other in the first transverse direction to thereby be placed in an actuated position, where the left and right joint regions are closer to each other, each of the left and right wall segments acquires a biasing force which biases the left and right wall segments towards a normal position, where the left and right joint regions are remote from each other. The left and right latch members respectively have left proximate and distal segments opposite to each other, and right proximate and distal segments opposite to each other. The left and right proximate segments are disposed to couple respectively with the right and left joint regions, such that the left and right proximate segments are respectively moved with the right and left joint regions in the first direction. The left and right distal segments are configured such that, when the left and right proximate segments are respectively moved with the right and left joint regions to the actuated position, the left and right distal segments are moved away from each other in the first direction so as to steer clear of the retained end through the access hole, thereby permitting the biasing member to bias the rear shell portion towards the rear position.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
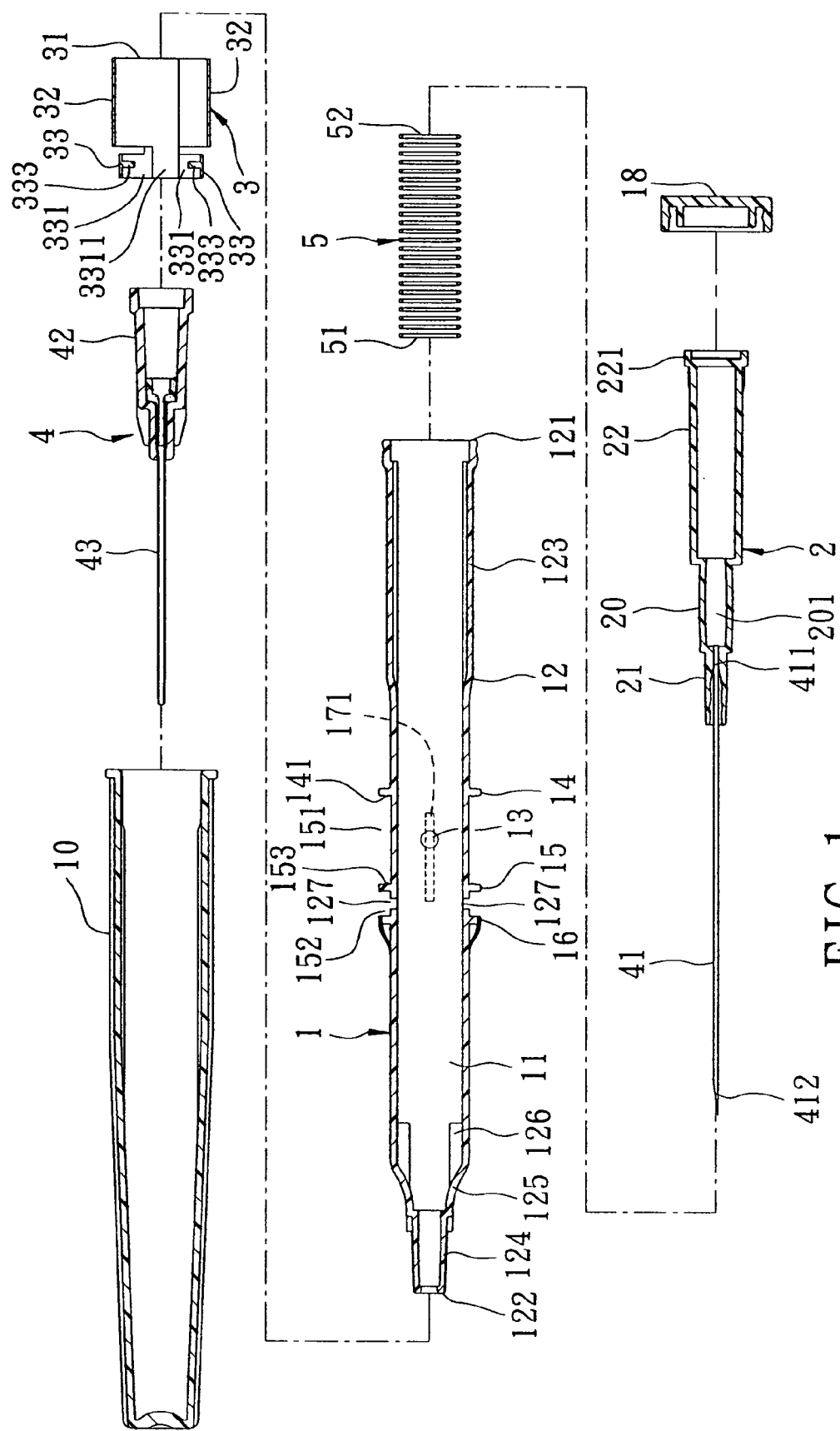
FIG. 1 is an exploded sectional view of a first preferred embodiment of an intravenous catheter introducing device according to this invention.

Before the present invention is described in greater detail, it should be noted that same reference numerals have been used to denote like elements throughout the specification.

Figure 2:
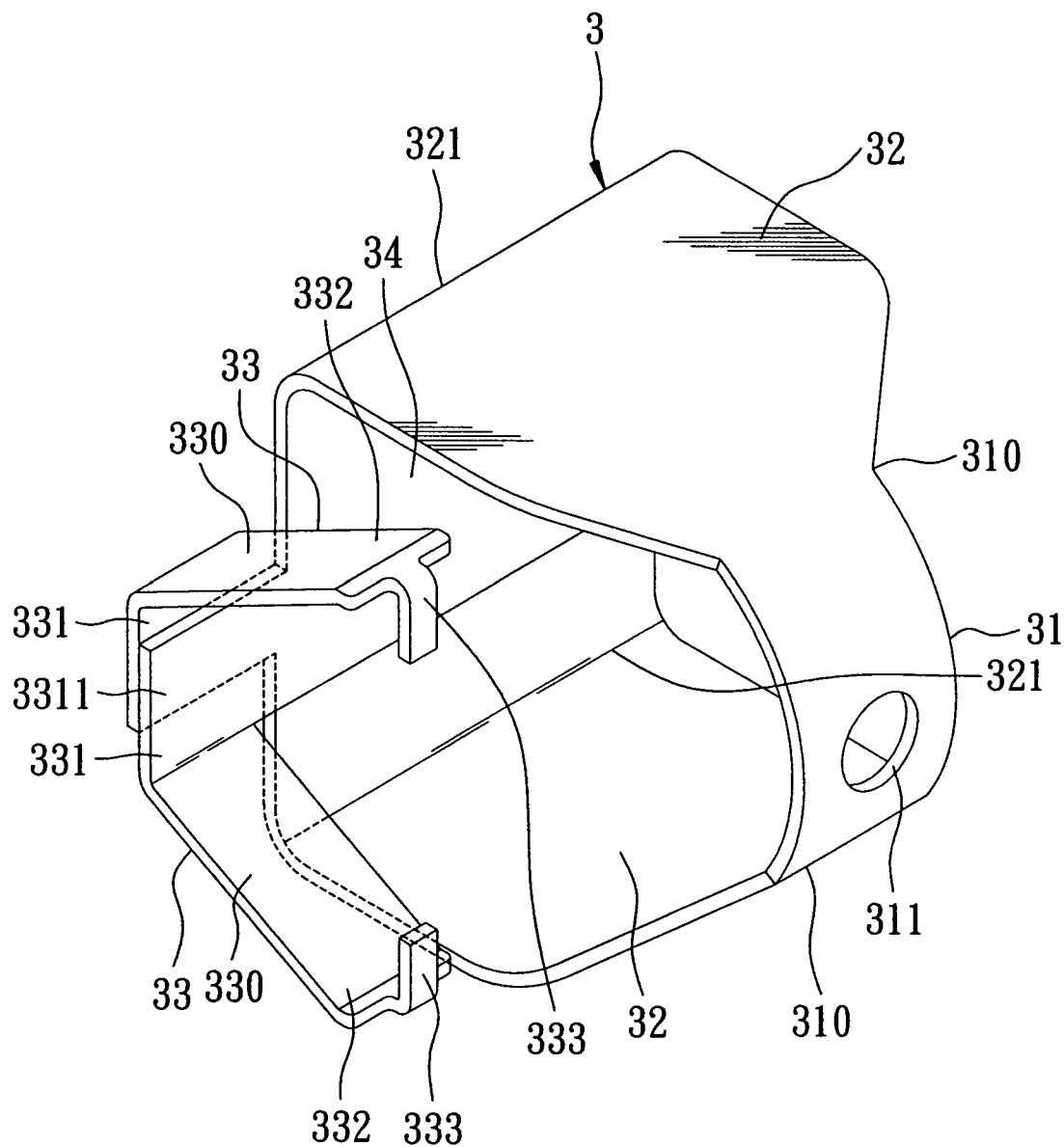
FIG. 2 is a perspective view of an easy release unit of the first preferred embodiment.
Figure 3:
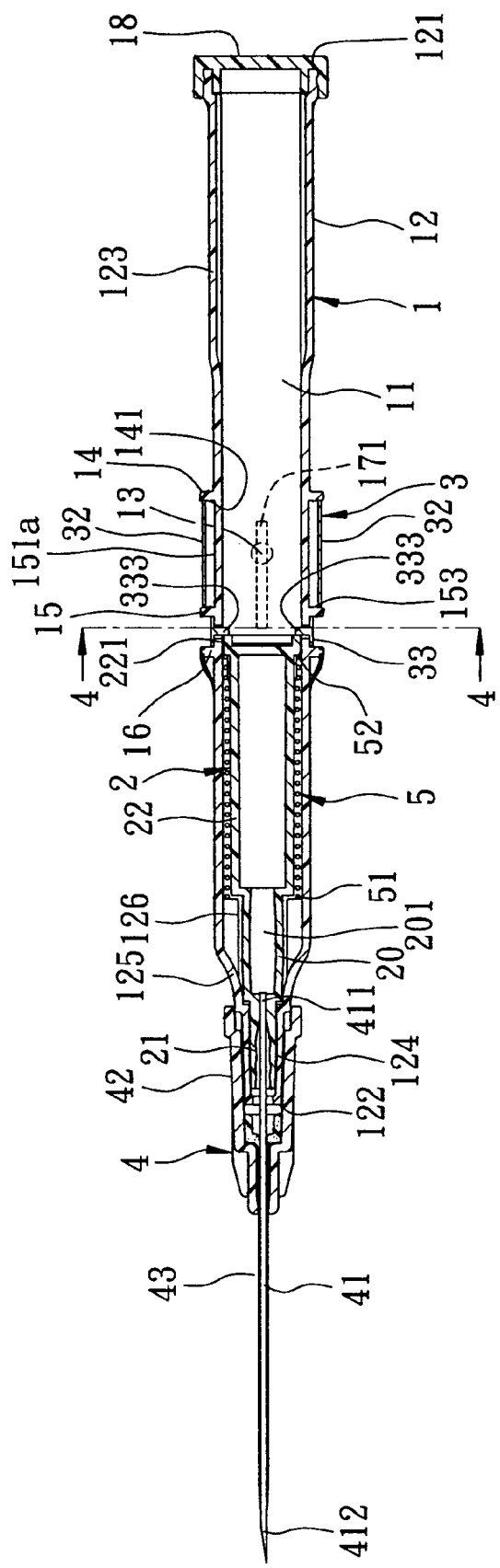
FIG. 3 is a sectional view of the first preferred embodiment in a position of use.

Referring to FIGS. 1 to 3, the first preferred embodiment of an intravenous catheter introducing device according to the present invention is shown to comprise a barrel 1, a needle cannula 41, a needle hub 2, a biasing member 5, a catheter connection assembly 4, a tip protector 10, and an easy release unit 3.

The barrel 1 has front and rear open ends 122,121 opposite to each other in a longitudinal direction, and a surrounding barrel wall 12 which interconnects the front and rear open ends 122,121. An end cap 18 is disposed to cover the rear open end 121. The surrounding barrel wall 12 includes a smaller-diameter wall portion 124 and a larger-diameter wall portion 123 which are opposite to each other in the longitudinal direction and which are proximate to the front and rear open ends 122,121, respectively, so as to define a shoulder portion 125 therebetween. The surrounding barrel wall 12 has an inner barrel wall surface which surrounds an axis in the longitudinal direction and which confines a passage 11 that is communicated with the front and rear open ends 122,121, and an outer barrel wall surface opposite to the inner barrel wall surface in radial directions relative to the axis. The outer barrel wall surface has an access hole which has left and right access hole portions 127 that are formed in the larger-diameter wall portion 123, that extend through the inner barrel wall surface, and that are diametrically opposite to each other in a first direction transverse to the longitudinal direction. The larger-diameter wall portion 123 has first and second ring portions 14,15 which extend radially and outwardly from the outer barrel wall surface, and which are spaced apart from each other in the longitudinal direction by a first annular groove 151. Two left and two right threshold barriers 141,153 extend respectively from the first and second ring portions 14,15 into the first annular groove 151, and cooperate with the outer barrel wall surface to define left and right retaining pits (151a). An engaging peg 13 is disposed on the outer barrel wall surface between the first and second ring portions 14,15. A third ring portion 16 extends radially and outwardly from the outer barrel wall surface, and is spaced apart from the second ring portion 15 in the longitudinal direction by a second annular groove 152. The left and right access hole portions 127 are disposed between the second and third ring portions 15,16. Furthermore, the larger-diameter wall portion 123 has a guiding spacer 171 which extends from the outer barrel wall surface radially.

The needle cannula 41 has a front segment terminating at a tip end 412, and a rear connecting end 411 opposite to the front segment along the axis.

The needle hub 2 includes a front holding portion 21 and a rear shell portion 22 disposed opposite to each other along the axis. The front holding portion 21 is surrounded by the smaller-diameter wall portion 124. The rear shell portion 22 is inserted into the passage 11 from the rear open end 121, and is disposed in and is slidable relative to the larger-diameter wall portion 123 along the axis between front and rear positions, which are respectively proximate to the front open end 122 and the rear open end 121. The front holding portion 21 holds the rear connecting end 411 of the needle cannula 41 such that, when the rear shell portion 22 is in the front position, the needle cannula 41 is placed in a position of use, where the front segment extends forwardly of the front open end 122 for ready use. When the rear shell portion 22 is in the rear position, the needle cannula 41 is placed in a disposal position, where the front segment retreats into the passage 11. The rear shell portion 22 surrounds the axis, and extends away from the front holding portion 21 to terminate at a retained end 221. The needle hub 2 further includes a transparent intermediate viewing-window portion 20 which is interposed between the front holding portion 21 and the rear shell portion 22 and which defines a blood-flow passage 201 that is in fluid communication with the needle cannula 41 for permitting viewing of blood flowing therein.

The biasing member 5 is interposed between the rear shell portion 22 and the inner barrel wall surface, and has an abutting end 51 which abuts against ribs 126 formed on the inner barrel wall surface of the larger-diameter wall portion 123 of the barrel 1 proximate to the shoulder 125, and an urging end 52 abutting against the retained end 221 of the rear shell portion 22 so as to bias the rear shell portion 22 toward the rear position. Hence, the biasing member 5 is disposed to surround the rear shell portion 22, and will not conceal the intermediate viewing-window portion 25 to obstruct viewing of flashback blood flow. As shown in FIG. 3, the left and right access hole portions 127 are disposed in the vicinity of the retained end 221 in the position of use.

The catheter connection assembly 4 includes a catheter hub 42 and a flexible tubular catheter 43.

The tip protector 10 is removably sleeved on the surrounding barrel wall 12 for shielding the needle cannula 41.

The easy release unit 3 includes an engaging wall segment 31, left and right squeezed wall segments 32, and left and right latch members 33.

Figure 4:
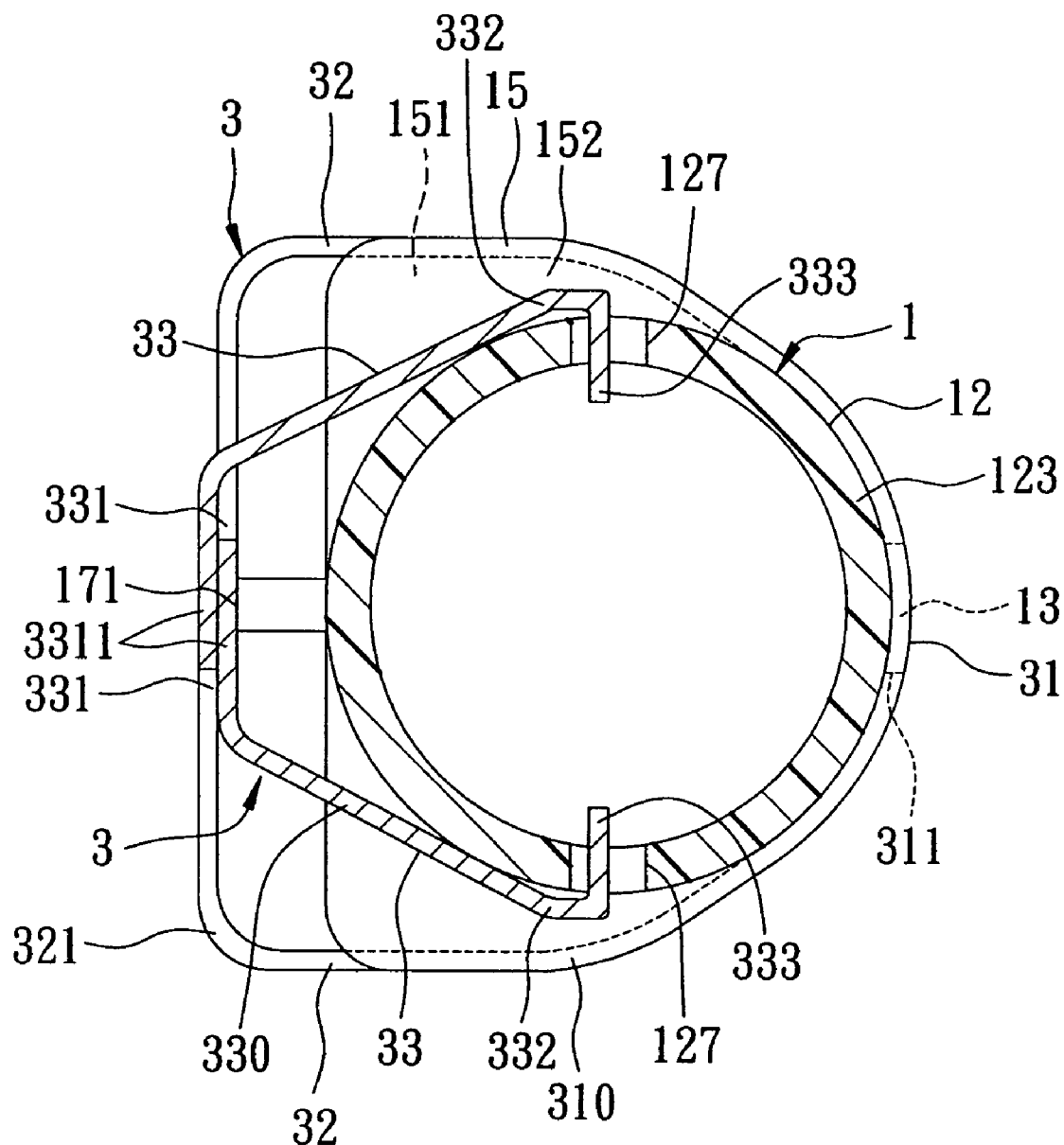
FIG. 4 is a cross-sectional view of the first preferred embodiment, taken along line 4-4 of FIG. 3.

The engaging wall segment 31 is configured to wrap about the outer barrel wall surface of the larger-diameter wall portion 123, and terminates at two boundary junctions 310. The engaging wall segment 31 has an engaging hole 311 to engage the engaging peg 13 so as to retain the engaging wall segment 31 on the larger-diameter wall portion 123, as shown in FIG. 4.

The left and right squeezed wall segments 32 are disposed outboard to the outer barrel wall surface to be fitted in the first annular groove 151 to thereby guard the easy release member 3 against displacement in the longitudinal direction, and are opposite to each other in a first direction transverse to the longitudinal direction. In this embodiment, the left and right squeezed wall segments 32 extend respectively from the boundary junctions 310 in the second direction transverse to both the longitudinal direction and the first direction, to respectively terminate at left and right joint regions 321. The left and right squeezed wall segments 32 are made of a flexible material such that, upon being squeezed towards each other in the first transverse direction to thereby be placed in an actuated position, where the left and right joint regions 321 are closer to each other, each of the left and right wall segments 32 acquires a biasing force which biases the left and right wall segments 32 towards a normal position, where the left and right joint regions 321 are remote from each other.

The left and right latch members 33 are elongated to respectively have left proximate and distal segments 331,332 opposite to each other, and right proximate and distal segments 331,332 opposite to each other. The left and right latch members 33 have left and right latch bodies 330, which are respectively interposed between the left proximate and distal segments 331,332, and between the right proximate and distal segments 331,332.

The left and right proximate segments 331 are disposed to couple respectively with the right and left joint regions 321 by left and right transit segments 34 such that the left and right proximate segments 331 are respectively moved with the right and left joint regions 321 in the first direction. The left and right proximate segments 331 are bent to form left and right overlapping portions 3311 which extend in the first direction, and which overlap each other in the second direction. As shown in FIG. 4, the guiding spacer 171 extends towards the left and right overlapping portions 3311 and in the longitudinal direction such that the left and right overlapping portions 3311 are guided to move in the first direction when the left and right joint regions 321 are moved between the normal and actuated positions.

The left and right distal segments 332 are fitted in the second annular groove 152 to guard the left and right latch members 33 against displacement in the longitudinal direction. The left and right distal segments 332 respectively have left and right fingers 333 which are respectively distal from the left and right latch bodies 330 and which extend in the first direction such that the left and right fingers 333 are moved with the right and left squeezed wall segments 32 in the first direction to be close to and away from each other. As shown in FIGS. 3 and 4, when the left and right squeezed wall segments 32 are in the normal position, the left and right fingers 333 extend respectively through the left and right access hole portions 127 to the passage 11 so as to hold the retained end 221 of the rear shell portion 22 of the needle hub 2 against the biasing action of the biasing member 5.

Figure 5:
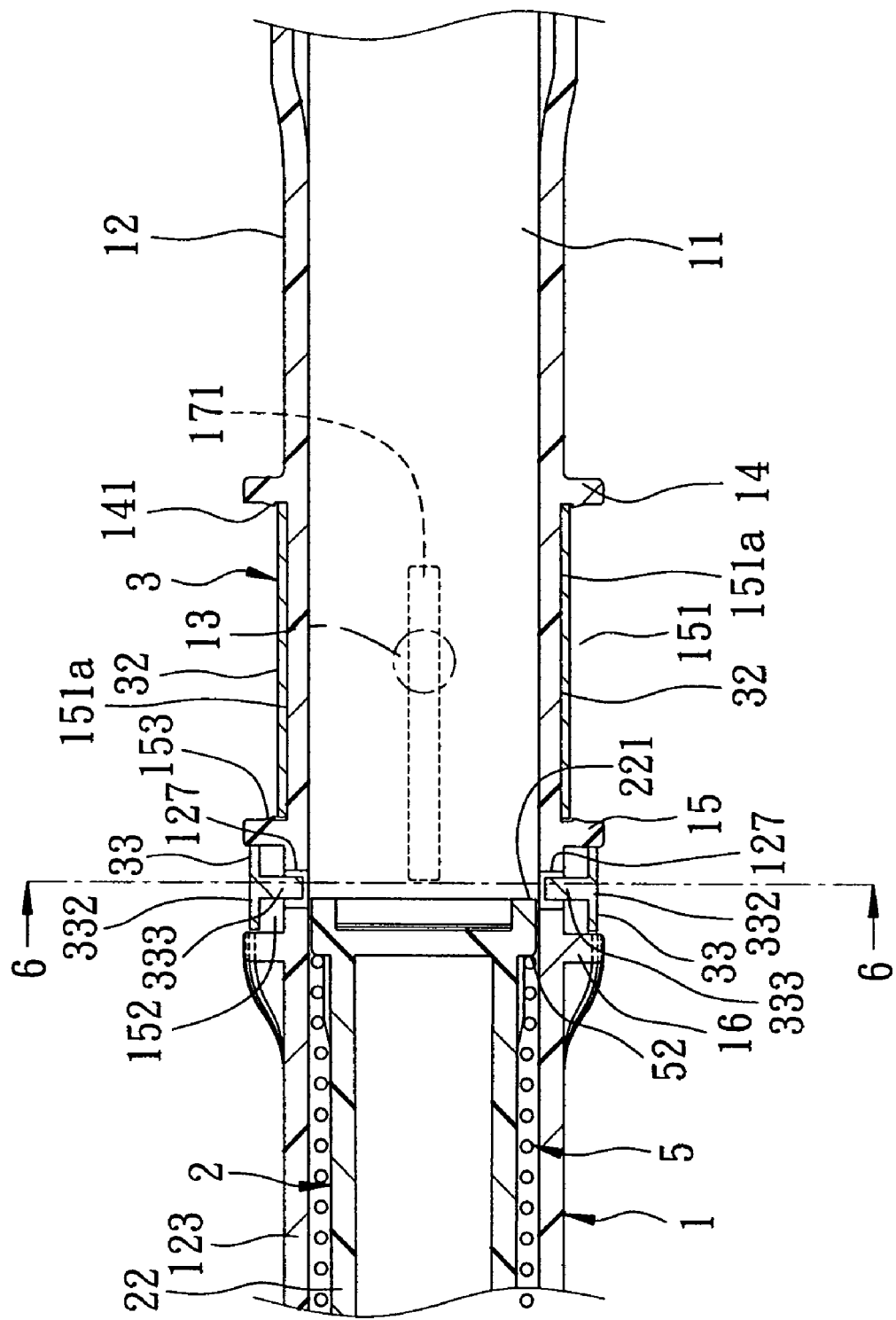
FIG. 5 is a fragmentary sectional view showing left and right squeezed wall segments of the easy release unit of the first preferred embodiment.
Figure 6:
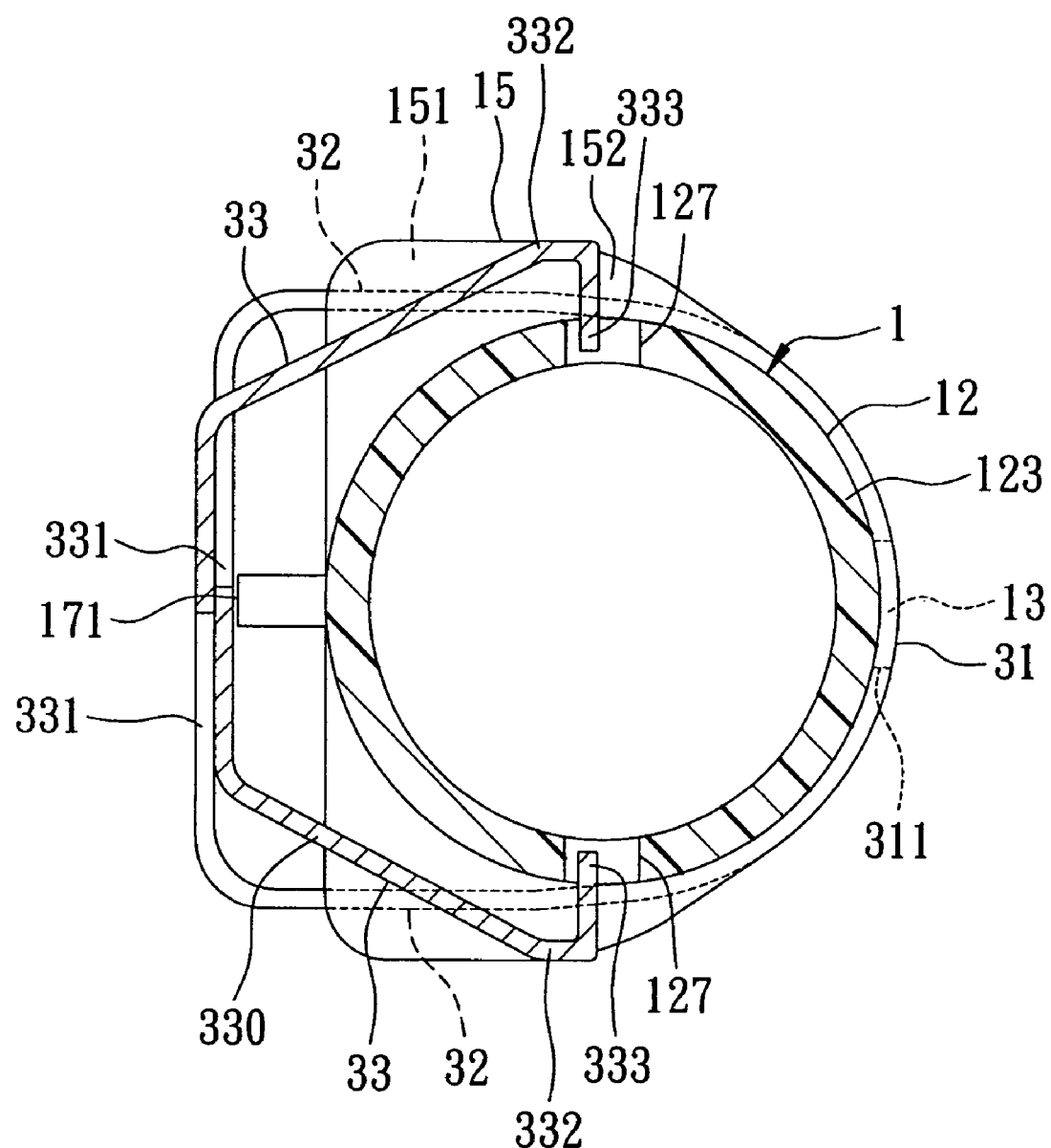
FIG. 6 is a cross-sectional view of the first preferred embodiment, taken along line 6-6 of FIG. 5.
Figure 7:
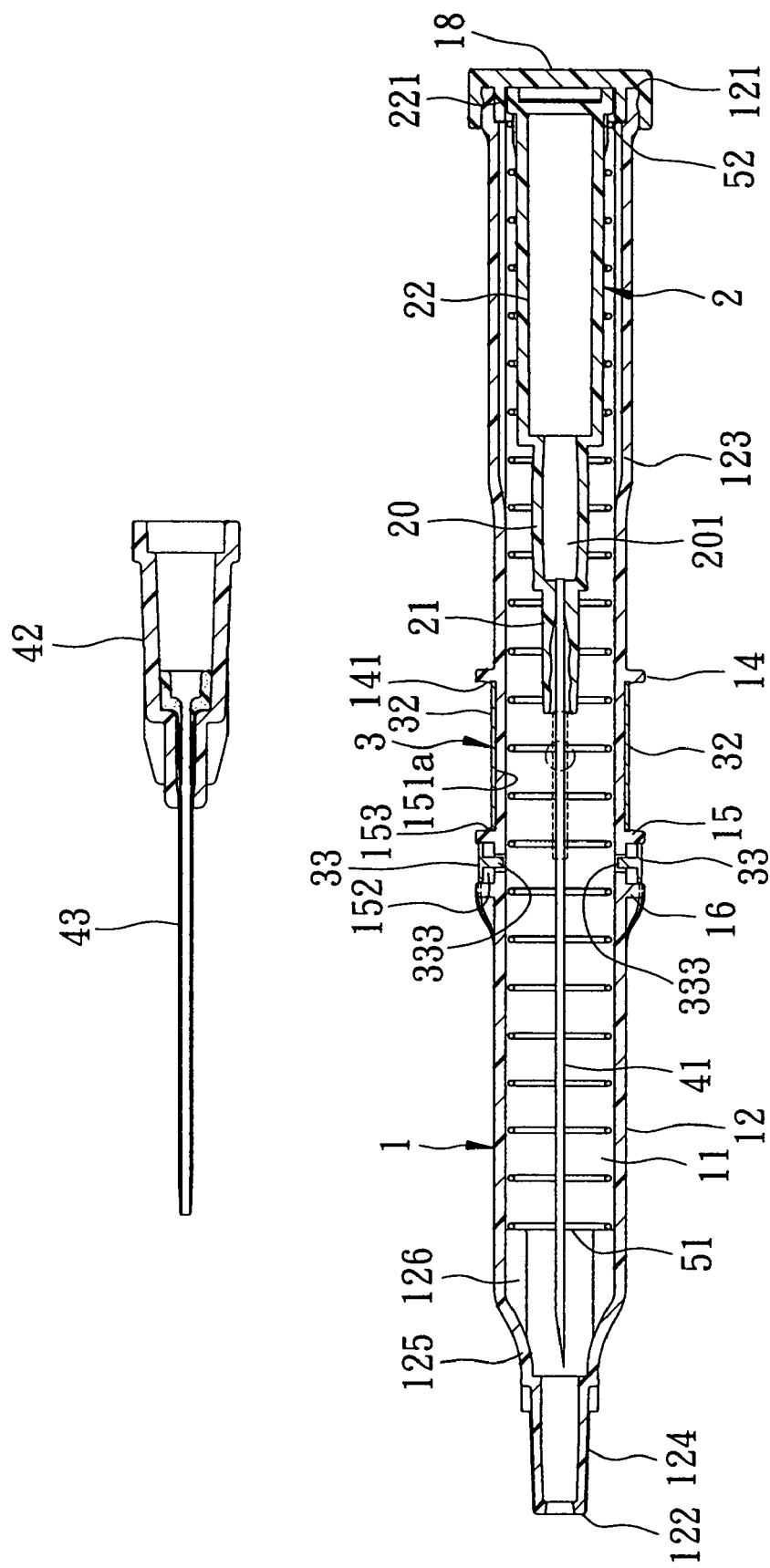
FIG. 7 is a sectional view of the first preferred embodiment in a retracted position.
Figure 8:
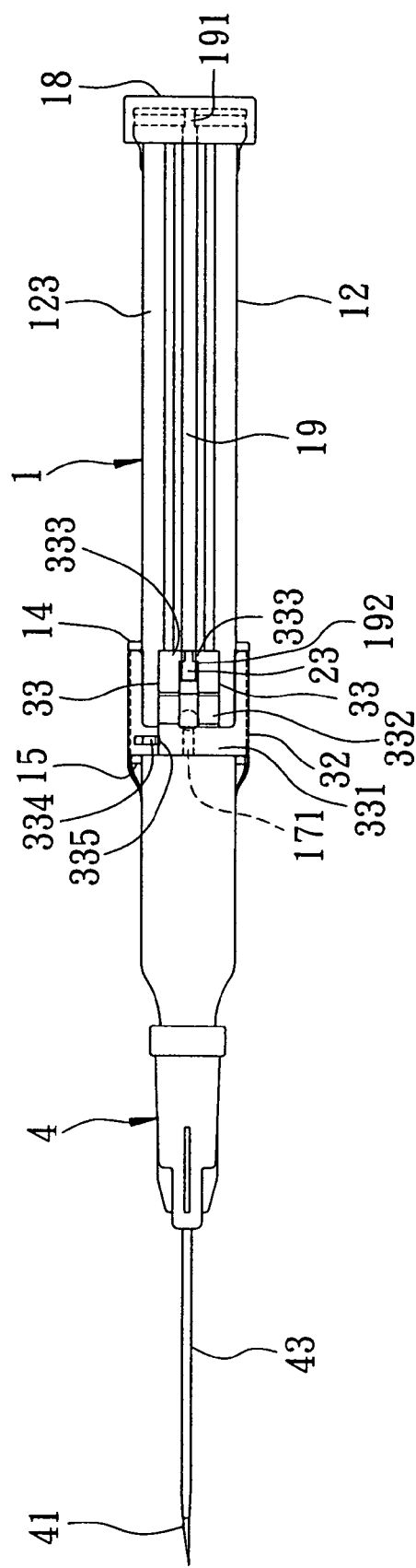
FIG. 8 is a schematic side view of a second preferred embodiment of an intravenous catheter introducing device according to this invention.

In use, the tip end 412 of the needle cannula 41 is inserted into the patient's vein so as to introduce the tubular catheter 43 into the vein. Blood flowing into the blood-flow passage 201 is visible so that the user can check whether the needle cannula 41 has been inserted properly into the vein. The user can then separate the catheter hub 42 from the barrel 1 with one finger of the hand that holds the barrel 1. Subsequently, the user can press the vein and the tubular catheter 43 with the other hand to complete the IV catheter introducing procedure. As shown in FIGS. 5 and 6, when the user symmetrically squeezes the left and right squeezed wall segments 32 to the actuated position, the left and right distal segments 332 are moved simultaneously away from each other in the first direction such that the left and right fingers 333 are moved away from the passage 11 to steer clear of the retained end 221 of the rear shell portion 22 to thereby permit the biasing member 5 to bias the rear shell portion 22 towards the rear position. Hence, the needle cannula 41 is moved smoothly to the disposal position to retreat into the passage 11, as shown in FIG. 7.

Moreover, once the left and right squeezed wall segments 32 are squeezed towards the outer barrel wall surface of the barrel 1, the left and right squeezed wall segments 32 are moved over the left and right threshold barriers 141,153, and are deformed so as to be urged into the left and right retaining pits (151a) immediately after slipping over the left and right threshold barriers 141,153. Thus, the left and right squeezed wall segments 32 are retained in the actuated position, thereby preventing reuse.

Figure 12:
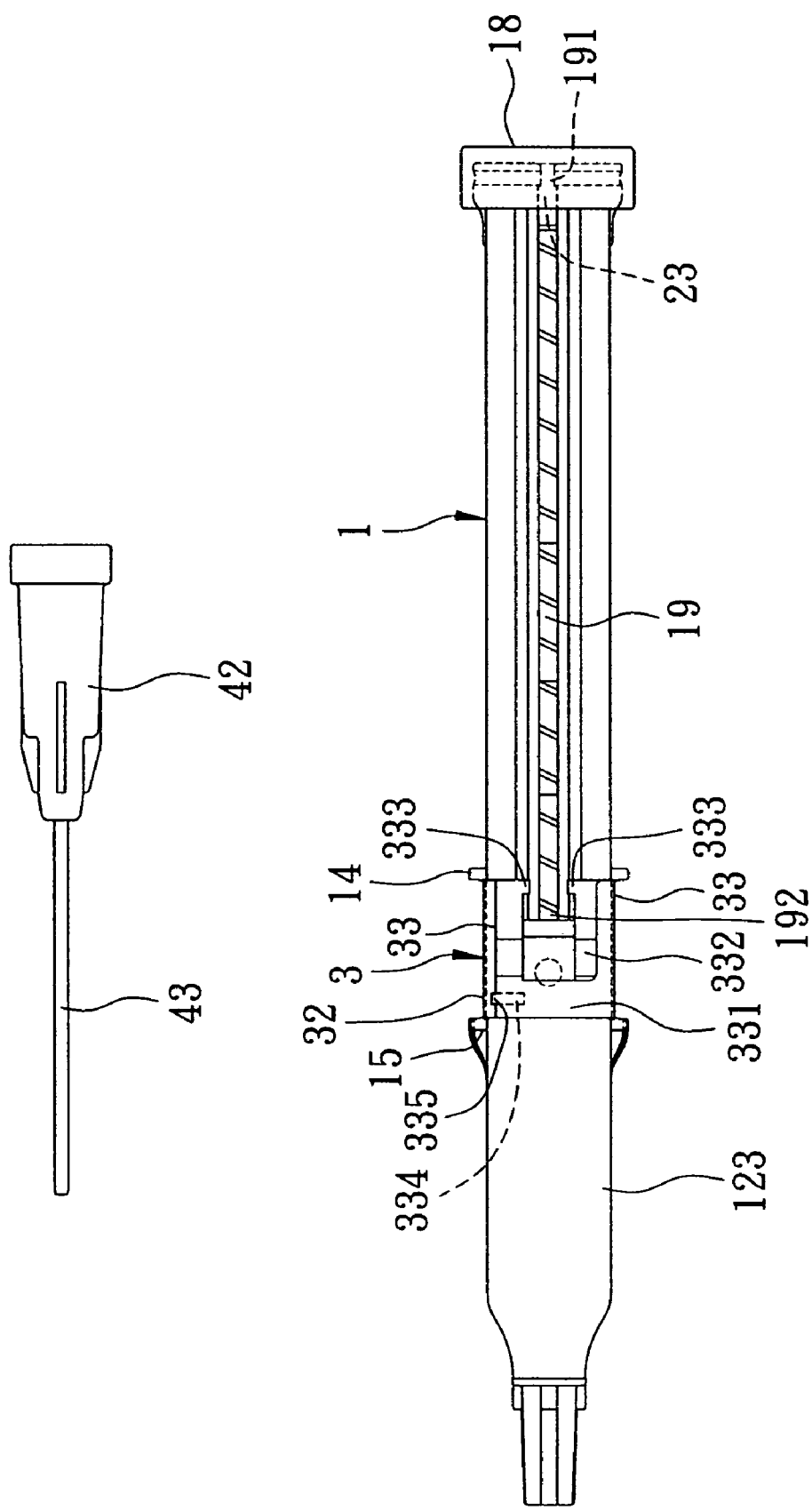
FIGS. 12 and 13 are respectively side and sectional views of the second preferred embodiment in a retracted position.
Figure 13:
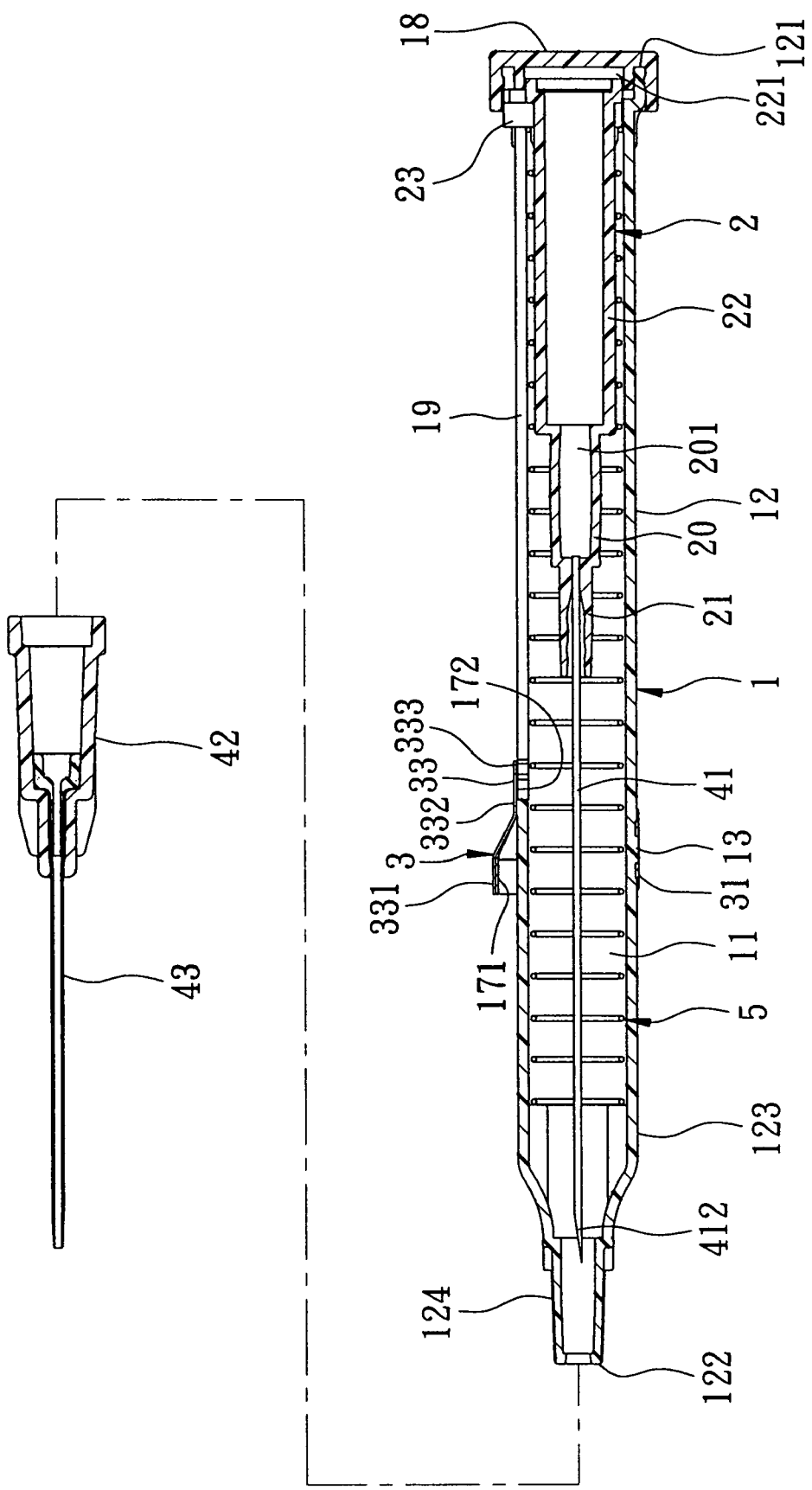
Figure 14:
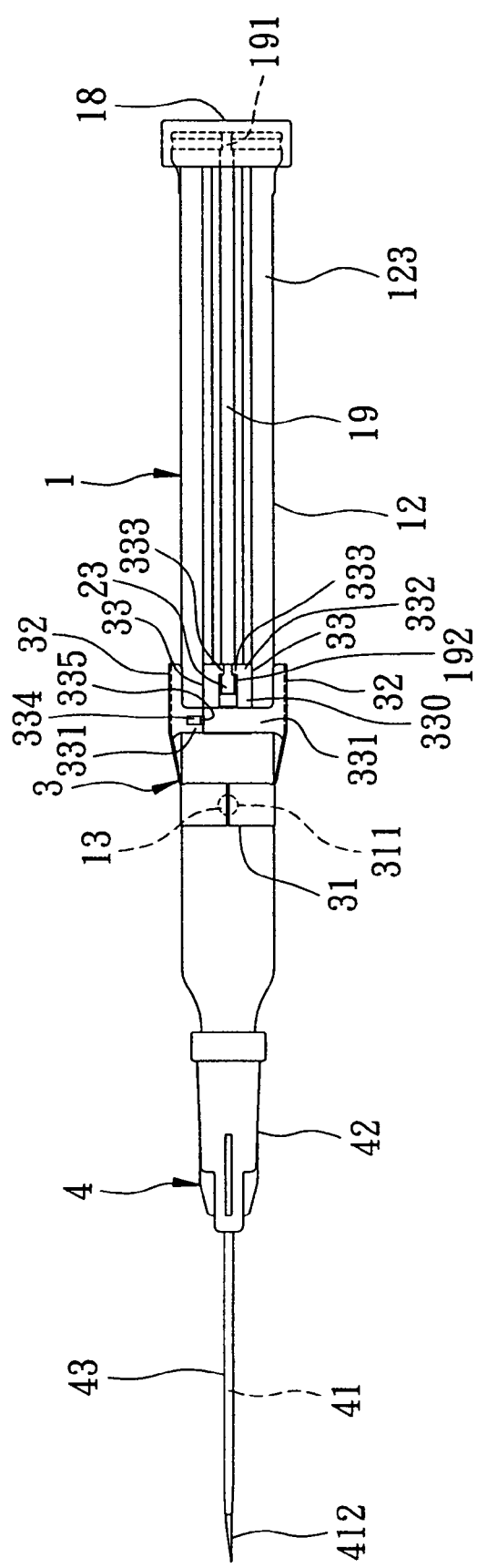
FIG. 14 is a schematic side view of a third preferred embodiment of an intravenous catheter introducing device according to this invention.
Figure 15:
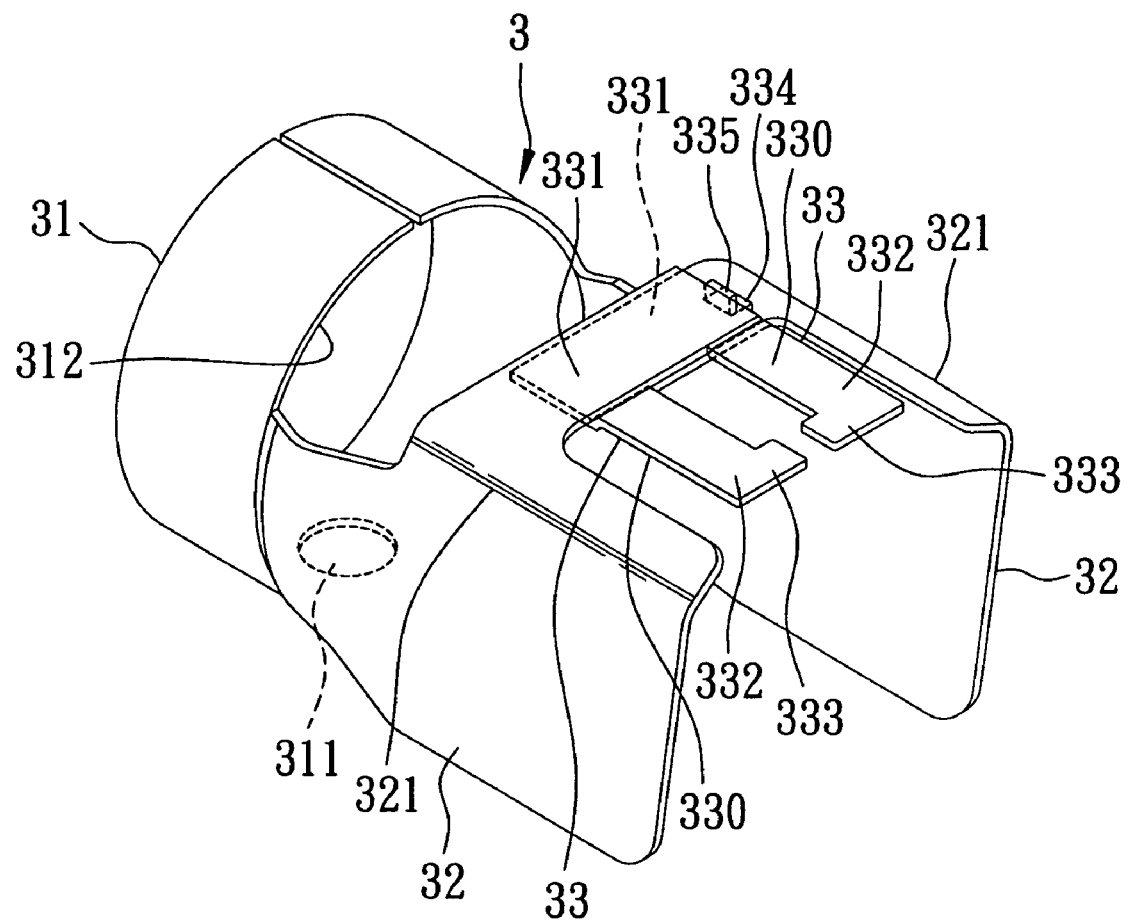
FIG. 15 is a perspective view of an easy release unit of the third preferred embodiment.
Figure 16:
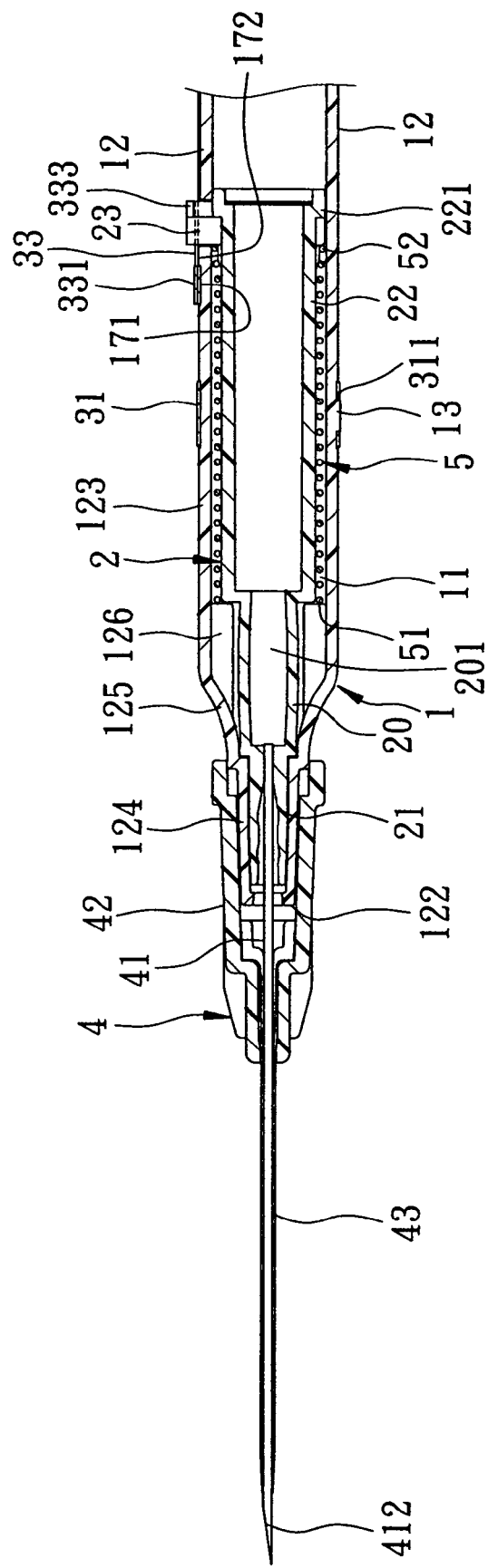
FIG. 16 is a fragmentary sectional view of the third preferred embodiment in a position of use.
Figure 17:
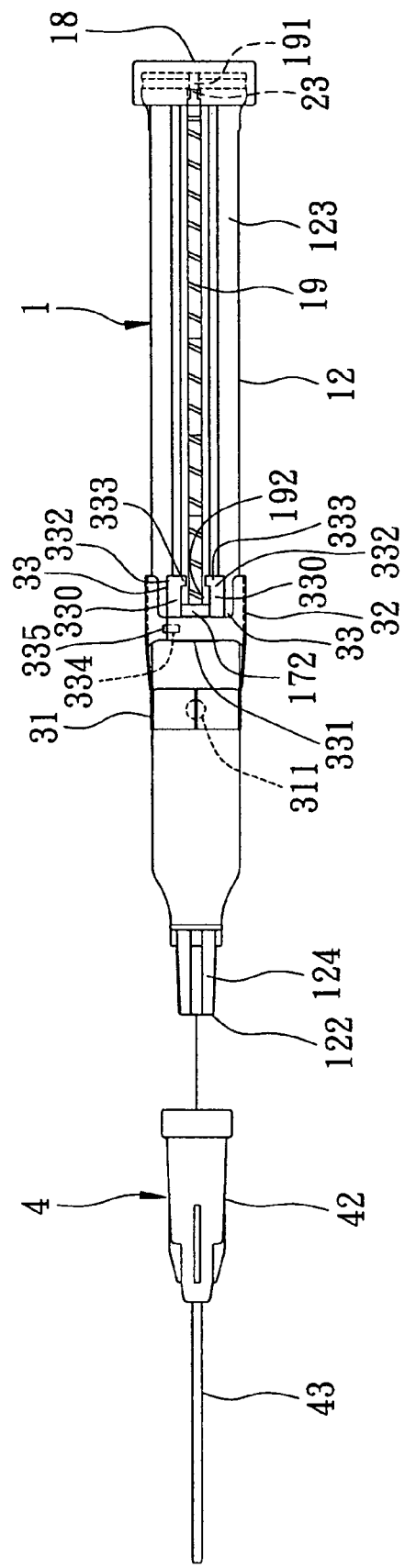
FIGS. 17 and 18 are respectively side and sectional views of the third preferred embodiment in a retracted position.
Figure 18:
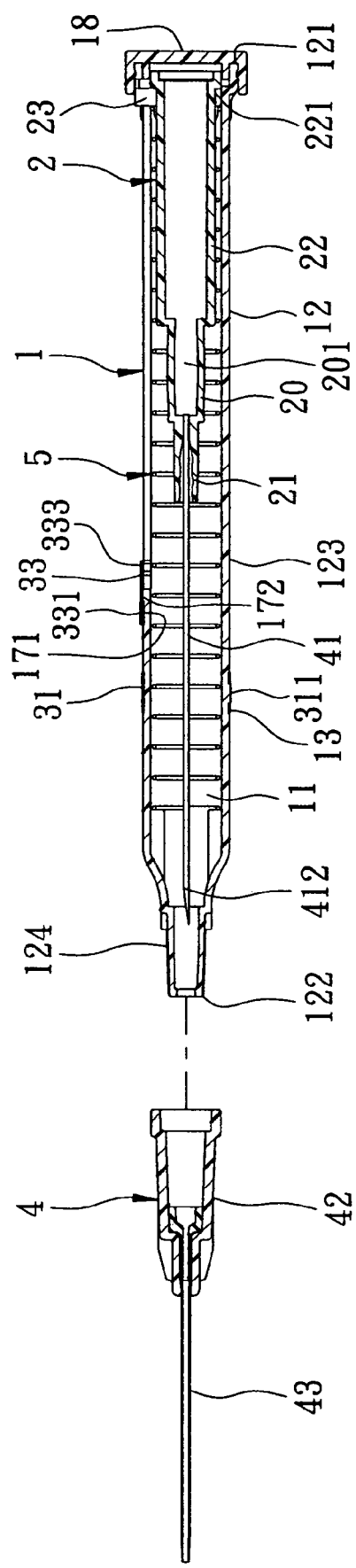

Referring to FIGS. 8 to 11, the second preferred embodiment of an intravenous catheter introducing device according to this invention is shown to be similar to the first embodiment in construction. The difference resides in that the outer barrel wall surface of the larger-diameter wall portion 123 has an elongated slot 19 which extends through the inner barrel wall surface and which is elongated from an access hole 192 rearwardly to terminate at a restricted hole 191. In addition, the needle hub 2 further includes a retained peg 23 which extends from the rear shell portion 22 and which is configured to extend through the access hole 192 such that the retained peg 23 is guarded by the left and right fingers 333 of the left and right latch members 33 against the biasing action of the biasing member 5 to hold the rear shell portion 22 in the front position. Moreover, when the left and right squeezed wall segments 32 are in the actuated position, i.e., the left and right squeezed wall segments 32 are squeezed towards each other, the left and right fingers 333 are moved away from each other to permit sliding movement of the retained peg 23 along the elongated slot 19 to the restricted hole 191 so as to move the rear shell portion 22 to the rear position. The end cap 18 is disposed to receive the retained peg 23 therein when the retained peg 23 is moved into the restricted hole 191 so as to disable the needle hub 2, i.e., to prevent the needle hub 2 from being moved back to the front position for reuse, as shown in FIGS. 12 and 13.

Figure 9:
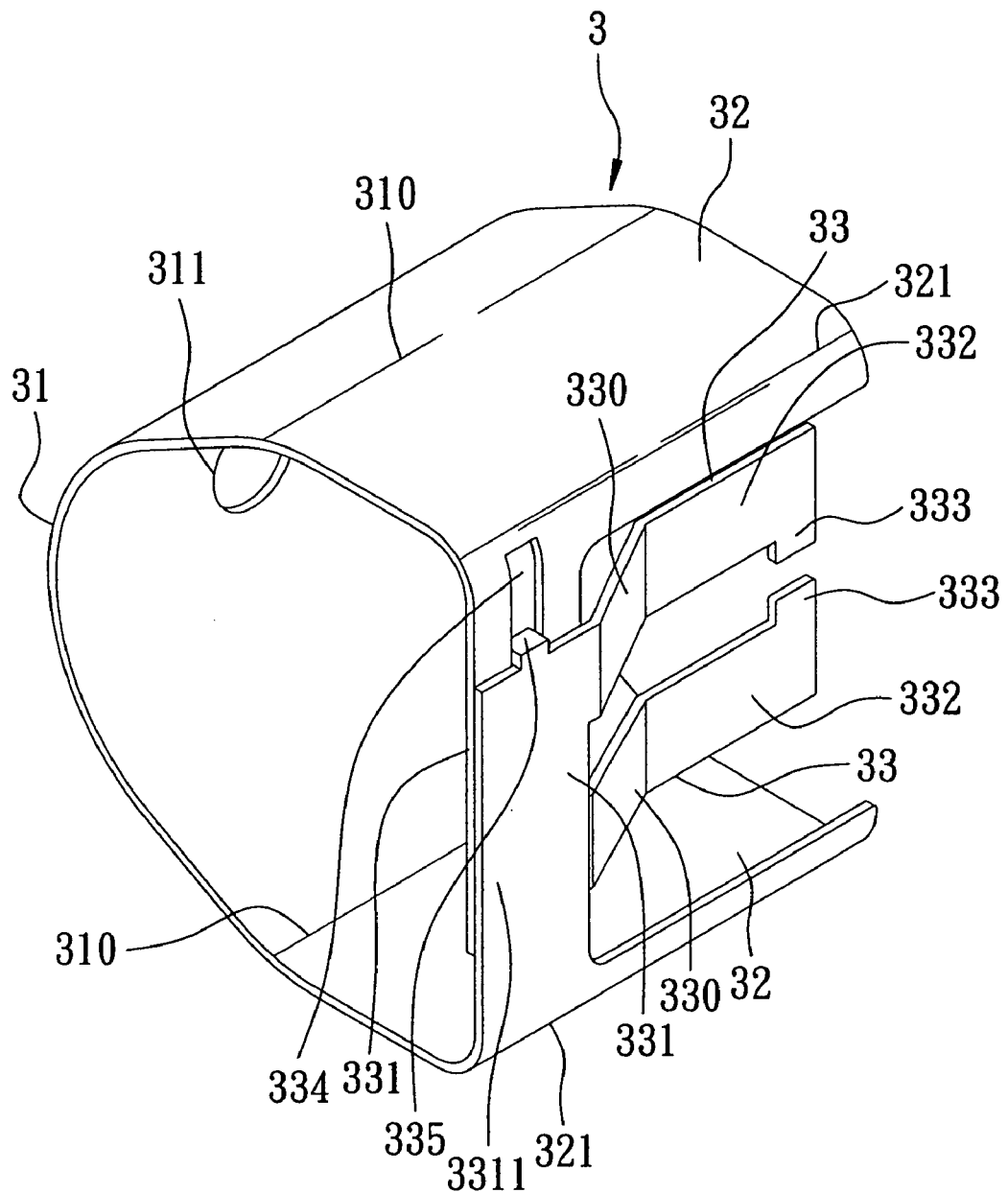
FIG. 9 is a perspective view of an easy release unit of the second preferred embodiment.
Figure 10:
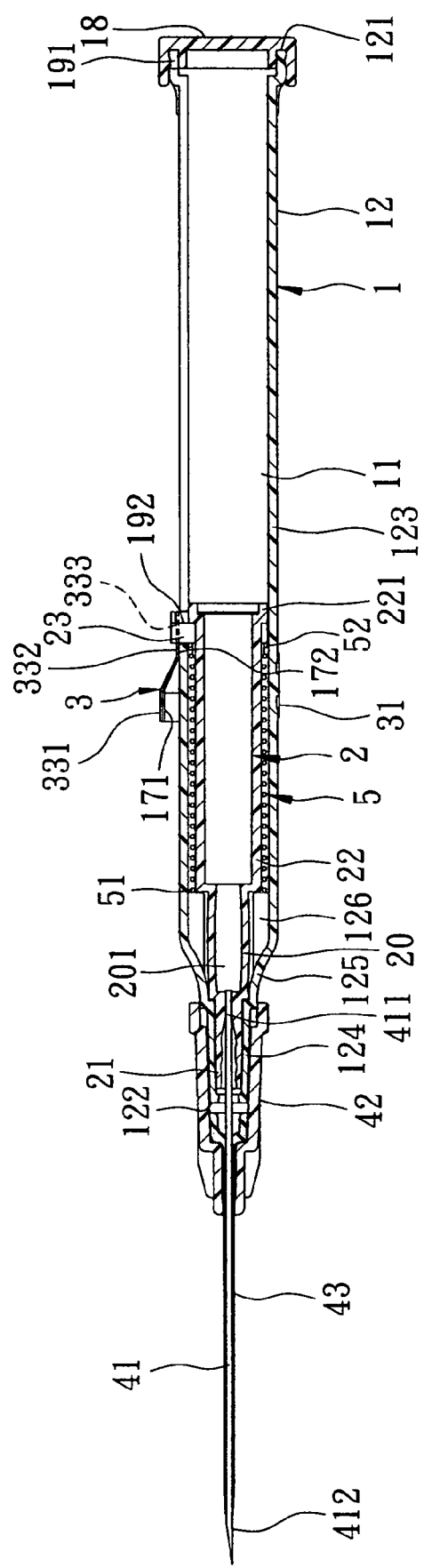
FIG. 10 is a sectional view of the second preferred embodiment in a position of use.
Figure 11:
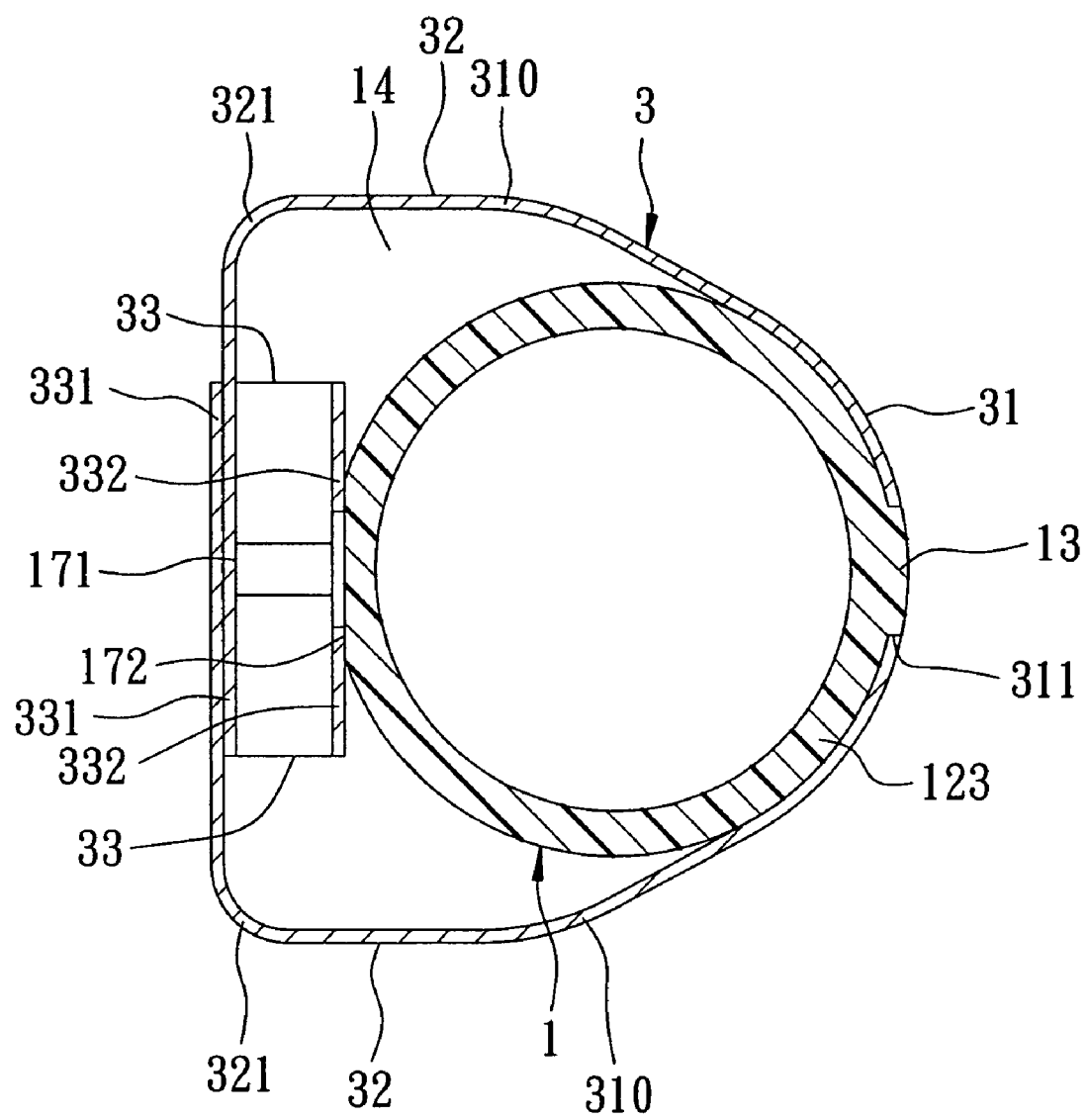
FIG. 11 is a cross-sectional view of a portion of the second preferred embodiment.

Furthermore, as shown in FIGS. 9 and 11, the easy release unit 3 of this embodiment is slightly different from that of the first embodiment. The engaging wall segment 31 of the easy release unit 3 is configured to wrap about the outer barrel wall surface of the barrel 1, and terminates at two boundary junctions 310. The left and right squeezed wall segments 32 extend respectively from the boundary junctions 310 in the second direction. The left and right proximate segments 331 of the left and right latch members 33 are bent to form left and right overlapping portions 3311, respectively, which extend in the first direction and which are respectively and integrally formed with the right and left joint regions 321. The easy release member 3 further has a guiding member which includes a key slot 334 that is formed in the right overlapping portions 3311 and that is elongated in the first direction, and a key 335 that is disposed on the left overlapping portion 3311 and that is slidable along the key slot 334 so as to ensure movement of the left and right overlapping portions 3311 in the first direction. The left and right distal segments 332 are disposed opposite to the left and right proximate segments 331 in the longitudinal direction, and are spaced apart from each other in the first direction to accommodate the retained peg 23 so as to permit the left and right fingers 333 to hold the retained peg 23 in the front position. Moreover, the larger-diameter wall portion 123 has a flat guiding surface 172 which extends radially and inwardly of the outer barrel wall surface so as to guide movement of the left and right distal segments 332 mounted thereon.

Referring to FIGS. 14 to 18, the third preferred embodiment of an intravenous catheter introducing device according to this invention is shown to be similar to the second embodiment in construction. The difference resides in that the engaging wall segment 31 of the easy release unit 3 is ring-shaped, is sleeved on the outer barrel wall surface of the barrel 1, and has a surrounding edge 312 surrounding the axis. The left and right squeezed wall segments 32 extend from the surrounding edge 312 in the longitudinal direction. The larger-diameter wall portion 123 has a flat guiding surface 172 which extends radially of the outer barrel wall surface so as to guide the movement of the left and right distal segments 332 mounted thereon.

During operation, the user can hold the barrel 2 with one hand and operate the left and right squeezed wall segments 32 with the same hand to cause the needle hub 2 to move to the rear position for drawing the used needle cannula 41 into the passage 11. As illustrated, the operation is controllable by the user and is convenient to conduct. Besides, undesirable accidents can be avoided. In addition, since the easy release unit 3 is formed by punching a flexible metal material, and is sleeved on the outer barrel surface of the barrel 1, the device of this invention has a simple construction, is easy to fabricate, and is compact in size.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

We claim:

1. An intravenous catheter introducing device comprising:
   a barrel having front and rear open ends opposite to each other in a longitudinal direction, and a surrounding barrel wall which interconnects said front and rear open ends, said surrounding barrel wall including a smaller-diameter wall portion and a larger-diameter wall portion which are opposite to each other in the longitudinal direction and which are respectively proximate to said front and rear open ends, said surrounding barrel wall having an inner barrel wall surface which surrounds an axis in the longitudinal direction and which confines a passage that is communicated with said front and rear open ends, and an outer barrel wall surface opposite to said inner barrel wall surface in radial directions relative to the axis, said outer barrel wall surface having an access hole which is formed in said larger-diameter wall portion and which extends through said inner barrel wall surface;
   a needle cannula having a front segment terminating at a tip end, and a rear connecting end opposite to said front segment along the axis;
   a needle hub including a front holding portion and a rear shell portion disposed opposite to each other along the axis, said front holding portion being surrounded by said smaller-diameter wall portion, said rear shell portion being inserted into said passage from said rear open end, and being slidable relative to said larger-diameter wall portion along the axis between front and rear positions which are respectively proximate to said front open end and said rear open end, said front holding portion holding said rear connecting end of said needle cannula such that, when said rear shell portion is in the front position, said needle cannula is placed in a position of use, where said front segment extends forwardly of said front open end for ready use, and when said rear shell portion is in the rear position, said needle cannula is placed in a disposal position, where said front segment retreats into said passage, said rear shell portion surrounding the axis and extending away from said front holding portion to terminate at a retained end, said needle hub further including an intermediate viewing-window portion which is interposed between said front holding portion and said rear shell portion and which defines a blood-flow passage that is in fluid communication with said needle cannula;
   a biasing member which is interposed between said rear shell portion and said inner barrel wall surface, and which is disposed to bias said rear shell portion toward the rear position, said access hole being disposed in the vicinity of said retained end in the position of use such that, by accessing said retained end through said access hole, said retained end is enabled to be held against the biasing action of said biasing member; and
   an easy release unit including
      an engaging wall segment configured to attach to said outer barrel wall surface,
      left and right squeezed wall segments which extend from said engaging wall segment to be outboard to said outer barrel wall surface, and which are opposite to each other in a first direction transverse to the longitudinal direction, said left and right squeezed wall segments being configured to extend in a second direction transverse to both the longitudinal direction and the first direction, and to terminate at left and right joint regions, respectively, said left and right squeezed wall segments being made of a flexible material such that, upon being squeezed towards each other in the first transverse direction to thereby be placed in an actuated position, where said left and right joint regions are closer to each other, each of said left and right wall segments acquires a biasing force which biases said left and right wall segments towards a normal position, where said left and right joint regions are remote from each other, and
      left and right latch members respectively having left proximate and distal segments opposite to each other, and right proximate and distal segments opposite to each other, said left and right proximate segments being disposed to couple with said right and left joint regions, respectively, such that said left and right proximate segments are moved respectively with said right and left joint regions in the first direction, said left and right distal segments being configured such that, when said left and right proximate segments are respectively moved with said right and left joint regions to the actuated position, said left and right distal segments are moved away from each other in the first direction so as to steer clear of said retained end through said access hole, thereby permitting said biasing member to bias said rear shell portion towards the rear position.

2. The intravenous catheter introducing device of claim 1, wherein said engaging wall segment and said outer barrel wall surface respectively have an engaging hole and an engaging peg to engage each other so as to retain said engaging wall segment on said outer barrel wall surface.

3. The intravenous catheter introducing device of claim 1, wherein said left and right latch members have left and right latch bodies that are respectively interposed between said left proximate and distal segments, and between said right proximate and distal segments, said left and right distal segments respectively having left and right fingers which are respectively distal from said left and right latch bodies and which extend in the first direction such that said left and right fingers are moved with said right and left squeezed wall segments in the first direction to be close to and away from each other.

4. The intravenous catheter introducing device of claim 3, wherein said access hole has left and right hole portions diametrically opposite to each other such that said left and right fingers extend respectively through said access hole portions so as to hold said retained end against the biasing action of said biasing member.

5. The intravenous catheter introducing device of claim 2, wherein said larger-diameter wall portion has first and second ring portions which extend radially and outwardly from said outer barrel wall surface, and which are spaced apart from each other in the longitudinal direction by a first annular groove that is configured to permit said left and right squeezed wall segments to be fitted therein so as to guard said easy release member in the normal position against displacement in the longitudinal direction.

6. The intravenous catheter introducing device of claim 5, wherein said larger-diameter wall portion has left and right threshold barriers which respectively extend from one of said first and second ring portions into said first annular groove, and which cooperate with said outer barrel wall surface to respectively define left and right retaining pits, said left and right threshold barriers being configured such that, once being squeezed to move towards said outer barrel wall surface, said left and right squeezed wall segments, by moving over said left and right threshold barriers, are deformed so as to be respectively urged into said left and right retaining pits immediately after slipping over said left and right threshold barriers.

7. The intravenous catheter introducing device of claim 6, wherein said larger-diameter wall portion has a third ring portion which extends radially and outwardly from said outer barrel wall surface, and which is spaced apart from said second ring portion in the longitudinal direction by a second annular groove that is configured to permit said left and right distal segments to be fitted therein so as to guard said left and right latch members against displacement in the longitudinal direction, said access hole being disposed between said second and third ring portions for access of said left and right fingers to said passage.

8. The intravenous catheter introducing device of claim 3, wherein said left and right proximate segments are bent to respectively form left and right overlapping portions which extend in the first direction, and which overlap each other in the second direction, said larger-diameter wall portion including a guiding spacer which extends from said outer barrel wall surface radially and towards said left and right overlapping portions, and which extends in the longitudinal direction such that said left and right overlapping portions are guided to move in the first direction when said left and right joint regions are moved between the normal and actuated positions.

9. The intravenous catheter introducing device of claim 8, wherein said left and right proximate segments are bent to form left and right overlapping portions which extend in the first direction and which are respectively and integrally formed with said right and left joint regions, said easy release member further including a guiding member which is disposed between said left and right overlapping portions so as to ensure movement of said left and right overlapping portions in the first direction.

10. The intravenous catheter introducing device of claim 9, wherein said guiding member includes a key slot which is elongated in the first direction, and a key which is slidable along said key slot.

11. The intravenous catheter introducing device of claim 3, wherein said outer barrel wall surface has an elongated slot which extends through said inner barrel wall surface and which is elongated from said access hole rearwardly to terminate at a restricted hole, said needle hub further including a retained peg which extends from said rear shell portion and which is configured to extend through said access hole such that said retained peg is guarded by said left and right fingers against the biasing action of said biasing member so as to hold said rear shell portion in the front position, and such that when said left and right squeezed wall segments are in the actuated position, said left and right fingers are moved away from each other to permit sliding movement of said retained peg along said elongated slot to said restricted hole so as to move said rear shell portion to the rear position.

12. The intravenous catheter introducing device of claim 11, wherein said left and right distal segments are disposed opposite to said left and right proximate segments in the longitudinal direction, and are spaced apart from each other in the first direction to accommodate said retained peg so as to permit said left and right fingers to hold said retained peg in the front position.

13. The intravenous catheter introducing device of claim 12, wherein said engaging wall segment is configured to wrap about said outer barrel wall surface, and terminates at two boundary junctions, said left and right squeezed wall segments extending respectively from said boundary junctions in the second direction.

14. The intravenous catheter introducing device of claim 11, wherein said engaging wall segment is ring-shaped, is sleeved on said outer barrel wall surface, and has a surrounding edge around the axis, said left and right squeezed wall segments extending from said surrounding edge in the longitudinal direction.

15. The intravenous catheter introducing device of claim 11, further comprising an end cap which is disposed to cover said rear open end and which is disposed to receive said retained peg therein when said retained peg is moved into said restricted hole.

16. The intravenous catheter introducing device of claim 3, wherein said engaging wall segment is configured to wrap about said outer barrel wall surface, and terminates at two boundary junctions, said left and right squeezed wall segments extending respectively from said boundary junctions in the second direction.

* * * * *